(12) United States Patent
Zwahlen et al.

(10) Patent No.: US 11,166,882 B2
(45) Date of Patent: Nov. 9, 2021

(54) PROCESS FOR PROVIDING FLUORESCENCE TO A DENTAL CERAMIC BODY

(71) Applicant: STRAUMANN HOLDING AG, Basel (CH)

(72) Inventors: Alexander Zwahlen, Bern (CH); Marc Stephan, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 16/857,260

(22) Filed: Apr. 24, 2020

(65) Prior Publication Data

US 2020/0247723 A1  Aug. 6, 2020

Related U.S. Application Data

(62) Division of application No. 15/549,321, filed as application No. PCT/EP2016/052543 on Feb. 5, 2016, now Pat. No. 10,662,120.

(30) Foreign Application Priority Data

Feb. 5, 2015 (EP) .................................... 15000339

(51) Int. Cl.
| | |
|---|---|
| *A61K 6/16* | (2020.01) |
| *C04B 41/87* | (2006.01) |
| *C04B 41/50* | (2006.01) |
| *C04B 35/486* | (2006.01) |
| *C04B 35/111* | (2006.01) |
| *C04B 35/638* | (2006.01) |
| *C04B 35/64* | (2006.01) |
| *A61K 6/802* | (2020.01) |
| *A61K 6/818* | (2020.01) |
| *A61K 6/70* | (2020.01) |
| *C01F 17/218* | (2020.01) |
| *C04B 41/00* | (2006.01) |
| *C04B 111/80* | (2006.01) |
| *C04B 111/00* | (2006.01) |

(52) U.S. Cl.
CPC .................. *A61K 6/16* (2020.01); *A61K 6/70* (2020.01); *A61K 6/802* (2020.01); *A61K 6/818* (2020.01); *C01F 17/218* (2020.01); *C04B 35/111* (2013.01); *C04B 35/486* (2013.01); *C04B 35/638* (2013.01); *C04B 35/64* (2013.01); *C04B 41/009* (2013.01); *C04B 41/5049* (2013.01); *C04B 41/87* (2013.01); *C01P 2002/54* (2013.01); *C04B 2111/00836* (2013.01); *C04B 2111/807* (2013.01); *C04B 2235/3225* (2013.01); *C04B 2235/3298* (2013.01); *C04B 2235/443* (2013.01); *C04B 2235/5436* (2013.01); *C04B 2235/604* (2013.01); *C04B 2235/6567* (2013.01); *C04B 2235/6587* (2013.01); *C04B 2235/661* (2013.01)

(58) Field of Classification Search
CPC .......... A61K 6/802; A61K 6/818; A61K 6/70; C04B 41/009; C04B 41/5049; C04B 35/111; C04B 35/486; C04B 35/64; C04B 35/638; C04B 2111/008; C04B 2111/36; C04B 2111/807; C04B 2235/3298; C04B 2235/6587
See application file for complete search history.

(56) References Cited

U.S. PATENT DOCUMENTS

| | | | |
|---|---|---|---|
| 5,770,225 A | 6/1998 | Parekh et al. | |
| 6,069,103 A * | 5/2000 | Kwon | C04B 35/486 501/103 |
| 6,827,892 B2 * | 12/2004 | Smirnova | H01M 8/1246 264/104 |
| 8,173,562 B2 * | 5/2012 | Holand | A61C 13/0022 501/103 |
| 2012/0012789 A1 | 1/2012 | Yamada et al. | |

FOREIGN PATENT DOCUMENTS

| | | | |
|---|---|---|---|
| FR | 2781366 | * | 1/2000 |
| FR | 2781366 A1 | | 1/2000 |
| WO | 2013/022612 A1 | | 2/2013 |
| WO | 2014/164199 A1 | | 10/2014 |
| WO | WO 2014164199 | * | 10/2014 |
| WO | 2015/084931 A1 | | 6/2015 |

OTHER PUBLICATIONS

Apr. 21, 2016 Search Report issued in International Patent Application No. PCT/EP2016/052543.
Apr. 21, 2016 Written Opinion issued in International Patent Application No. PCT/EP2016/052543.
May 29, 2020 Extended European Search Report issued in European Patent Application No. 20157671.7.

* cited by examiner

*Primary Examiner* — C Melissa Koslow
(74) *Attorney, Agent, or Firm* — Oliff PLC

(57) ABSTRACT

A process for providing fluoresence to a dental ceramic body by treating at least a portion of the outer surface of the dental ceramic body or a precursor thereof with a bismuth containing substance, characterized by the steps of placing the dental ceramic body or the precursor thereof into a closeable container, in particular a crucible; generating a bismuth containing atmosphere in the container and exposing at least a portion of the outer surface of the dental ceramic body or of the precursor to the bismuth containing atmosphere at a temperature above 1000° C.

6 Claims, 2 Drawing Sheets

PROCESS FOR PROVIDING FLUORESCENCE TO A DENTAL CERAMIC BODY

Figure 1:
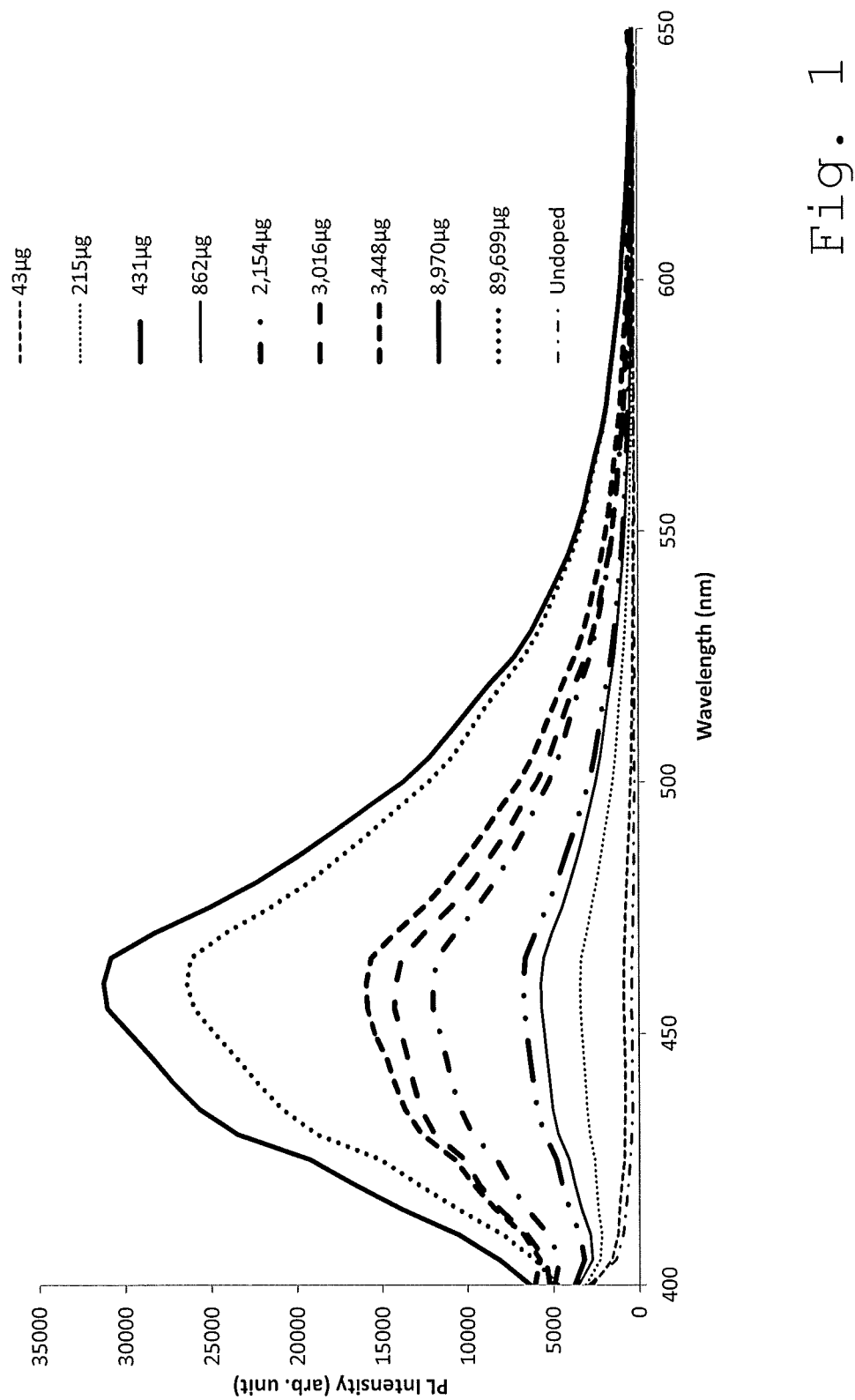

This is a Division of application Ser. No. 15/549,321 filed Aug. 7, 2017, now U.S. Pat. No. 10,662,120, which is a National Phase of International Application No. PCT/EP2016/052543 filed Feb. 5, 2016, which in turn claims the benefit of European Application No. 15000339.0 filed Feb. 5, 2015. The disclosure of the prior applications is hereby incorporated by reference herein in its entirety.

The present invention relates to a process for providing fluorescence to a dental ceramic body.

The present invention further relates to a dental ceramic body, in particular to a prosthetic element for use in a dental restoration.

The aestethics of a dental restoration depends to an important part on its translucency and color, which ideally closely resemble the one of a natural tooth.

From an aestethical point of view, ceramics, such as zirconia and/or alumina ceramics, are particularly well suited as restorative materials, because of their ability to provide excellent cosmetic results owed to their colour and their adequate reflection and transmission of light. In addition, these ceramics are biocompatible and exhibit good mechanical strength when subjected to masticatory efforts.

In order to adequately mimick the appearance of a natural tooth, also its inherent luminescence, in particular the of the dentin tissue, needs to be taken into account.

Fluorescence refers to the phenomenon of light being emitted by a substance that has absorbed light or other electromagnetic radiation. Typically, the emitted light is of longer wavelength and, therefore, lower energy than the absorbed radiation.

In a natural tooth, the fluorescent properties are such that ultraviolet light is absorbed and visible light in the blue spectrum is emitted. Due to the high amount of light in the blue spectrum generated, a natural tooth often appears whiter and brighter in daylight than restorative materials.

Efforts have, thus, been taken to adapt the fluorescence intensities of restorative materials as closely as possible to that of human teeth, in particular the enamel and dentin tissue, to ensure an acceptable reproduction of these qualities in aestethic restorations.

US 2012/0012789, for example, relates to a fluorescent zirconia material as a dental material comprising a fluorescent component and emitting fluorescence when excited with a light of a predetermined wavelength. The fluorescent component includes a fluorescent material including at least one kind of $Y_2SiO_5$:Ce, $Y_2SiO_5$:Tb, (Y, Gd, Eu)$BO_3$, $Y_2O_3$:Eu, YAG:Ce, $ZnGa_2O_4$:Zn and $BaMgAl_{10}O_{17}$:Eu. According to US 2012/0012789, the fluorescent material is mixed in the form of fluorescent powder to the raw material powder.

FR 2 781 366 A1 relates to a dental ceramic composition essentially consisting of yttria-stabilized zirconia, a colouring filling material and impurities, the colouring filling material consisting of $Fe_2O_3$, $Bi_2O_3$ and $CeO_2$. The content of $Fe_2O_3$ is according to FR 2 781 366 A1 preferably between 0.03 wt.-% and 0.1 wt.-%.

Further, WO 2014/164199 deals with the problem of mimicking the natural tooth appearance in dental restorations taking into account the individual degrees of color and brightness of the hard dental tissues, e.g. of enamel and dentin. In this regard, WO 2014/164199 suggests a solution for colouring and imparting fluorescence to a zirconia dental article, the solution comprising a solvent, a colouring agent comprising ions selected from Tb, Er, Pr, Mn and combinations thereof, and a fluorescing agent comprising ions of Bi.

A solution for treating the surface of a pre-sintered dental ceramic is further disclosed in WO 2013/022612. Specifically, WO 2013/022612 aims at avoiding a complete diffusion of the composition into the pores of the pre-sintered dental ceramic so that a defined application of the colouring solution can be accomplished. To this end, WO 2013/022612 suggests a non-water based solution comprising a solvent other than water, an effect agent causing either colouring, providing fluorescence or a combination thereof, and a complexing agent.

Both the solutions suggested in WO 2013/022612 and in WO 2014/164199 are to be applied on a porous dental article, typically by means of a brush. According to WO 2014/164199, the preferred time of treatment is preferably 1 to 3 minutes.

Often, there is the case that the dental ceramic already has the desired colour, but needs to be provided with fluorescence only, i.e. without changing the colour. If this is to be achieved by treating the dental ceramic with a solution according to e.g. WO 2013/022612, drying of the treated dental ceramic is typically required in order to avoid i.a. inhomogeneous colour effects. Inhomogeneities in the colouring can in particular arise from the method of applying the solution, as it is for example the case when using a brush.

According to both WO 2013/022612 and WO 2014/164199, drying of the treated ceramic article typically takes about 1 to 3 hours. Overall, the treatment of the ceramic with the solution and and the drying of the solution results in a time-consuming process.

In order to streamline the process of providing fluorescence to a dental ceramic body, a time-saving but nevertheless simple process would be desirable.

The problem to be solved by the present invention is, thus, to provide a process for providing fluorescence to a dental ceramic body in a simple and time-saving manner.

The problem is solved by the process for providing fluorescence to a dental ceramic body disclosed herein. Preferred embodiments of the invention are defined in the claims.

The present invention relates to a process for providing fluorescence to a dental ceramic body by treating at least a portion of the outer surface of the dental ceramic body or a precursor thereof with a bismuth containing medium.

The process is characterized by the steps of
a) placing the dental ceramic body or the precursor thereof into a closeable container, in particular a crucible;
b) generating a bismuth containing atmosphere in the container and
c) exposing at least a portion of the outer surface of the dental ceramic body or of the precursor to the bismuth containing atmosphere at a temperature above 1000° C.

It has surprisingly been found that at a temperature above 1000° C., bismuth, in particular in the form of bismuth oxide, penetrates into the dental ceramic body in an amount sufficient for providing fluorescence closely resembling the one of a natural tooth. In this context, bismuth can also be referred to as a "dopant".

Specifically, the dopant bismuth diffuses into the ceramic material, whereby it moves through the crystal lattice of the ceramic material. This can take place in different ways, e.g. by empty space diffusion, whereby the dopant fills an empty place present in the crystal lattice. Alternatively or additional, the dopant can diffuse by inter lattice diffusion, whereby it moves in-between the atoms in the crystal lattice, or by changing of places, whereby the dopant is located in the crystal lattice and exchanged with a crystal lattice atom.

Unlike the processes suggested in the state of the art mentioned above, in particular in WO 2013/022612 and in WO 2014/164199, the process of the present invention allows providing fluorescence to the body without applying a solution comprising the fluorophor. The time-consuming steps of applying and drying the solution can thus be obviated.

Specifically and as will be discussed in further detail below, the present invention allows the process of providing fluorescence to be integrated in the sintering step and/or at least one of the post-sintering steps, e.g. the white firing, for preparing the dense ceramic body. Due to the fact that bismuth, specifically in the form of bismuth oxide, is incorporated into the ceramic material simultaneously with at least one of the process steps that are normally performed for preparing the ceramic body, a very time-saving process can ultimately be achieved.

In addition, the present invention allows a homogeneous fluorescence to be provided, given the fact that the entire surface to be exposed is virtually facing the same atmosphere during step c). Inhomogeneities that might arise when e.g. a fluorophor containing solution is applied by means of a brush, i.e. the typical application method according to WO 2013/022612, can thus be avoided.

Due to the fluorophor being bismuth, specifically in the form of bismuth oxide, a broad excitation spectrum as well as an emission spectrum resembling the one of a natural tooth can be achieved. In particular, a broad excitation spectrum and a whitish-blue emission can be achieved.

Further, the present invention allows the desired fluorescence to be combined with a colouring of the dental ceramic body, which is typically performed before providing fluorescence. In particular, the desired fluorosence can be applied on a coloured dental ceramic body by introducing bismuth, specifically in the form of bismuth oxide, in an amount at which there is no or no substantial discoloration.

As will be explained in more detail below, the fluorescence intensity can be easily tuned by adapting the amount of bismuth contained in the bismuth containing atmosphere.

Although the present invention allows bismuth, specifically in the form of bismuth oxide, to penetrate into the ceramic material in an amount sufficient to provide the desired fluorescence, the amount can still be kept low enough not to have a negative impact on the mechanical stability of the dental ceramic body. In particular, the tetragonal phase stability of zirconia is not influenced in a negative way by the doping with bismuth.

In addition, the biocompatibility of the dental ceramic body is not affected by the process of the present invention.

The term "dental ceramic body" as used in the context of the present invention relates to any ceramic body suitable in the field of dentistry. The term can relate both to a pre-sintered ceramic body (often referred to as the "porous ceramic body", to a sintered ceramic body (often referred to as the "dense ceramic body") or to a ceramic body after at least one post-sintering step, e.g. white firing. Accordingly, the term "precursor" can in particular relate to the green body obtained by pressing the respective ceramic powder.

Preferably, the dental ceramic body comprises or essentially consists of zirconia and/or alumina. In particular zirconia shows outstanding properties with regard to aesthetic appearance and mechanical properties.

It is further preferred that the ceramic material of the body, in particular zirconia and/or alumina, is devoid of any metal that might quench the fluorescent properties provided by bismuth. Preferably, the ceramic material is devoid of iron (Fe).

According to a particular preferred embodiment, the dental ceramic body comprises or essentially consists of yttria-stabilized zirconia. By using yttria-stabilized zirconia, a body having a particularly high mechanical strength can be achieved.

In this regard, the term "yttria-stabilized zirconia" encompasses—besides purely yttria-stabilized zirconia—any yttria-stabilized zirconia that is co-stabilized with a co-stabilizing agent, such as cerium, calcium, erbium and/or magnesium or their respective oxides.

Also, the term "yttria-stabilized zirconia" encompasses both a material based on zirconia particles co-precipitated with yttria as well as a material based on yttria-coated zirconia particles.

An example of an yttria-stabilized zirconia based on zirconia particles co-precipitated with yttria is $ZrO_2$-TZP/TZP-A Bio-HIP® ($ZrO_2$) Bioceramic of Metoxit AG, Switzerland. The composition of this ceramic material comprises 92.1 to 93.5 weigth-% $ZrO_2$, 4.5 to 5.5 weigth-% $Y_2O_3$, 1.8 to 2.2 weight-% $HfO_2$ and 0.25 weight-% $Al_2O_3$. It offers a particularly high mechanical stability and strength, in particular when prepared by hot isostatic pressing or by sintering with subsequent hot isostatic densification. A detailed description of the ceramic material is given in U.S. Pat. No. 6,165,925, the disclosure of which is incorporated herein in its entirety by reference.

Apart from yttria-stabilized zirconia, also e.g. ceria-stabilized or magnesia-stabilized zirconia as well as zirconia stabilized with strontium, ytterbium, gadolinium, calcium, erbium or neodymium or their oxides, respectively, are thinkable and also encompassed by the term "dental ceramic" according to the present invention.

The dental ceramic body or the precursor thereof is according to step a) placed into a closeable container, particularly a crucible, more particularly a sintering crucible.

After step a), i.e. after placing the dental ceramic body or the precursor thereof into the container, a bismuth containing atmosphere is generated in the container in step b).

Typically, the bismuth containing atmosphere is generated by the evaporation of a bismuth compound from a bismuth source containing the bismuth compound. In this regard, it is preferred that the bismuth source is placed in a region of the container other than the region where the dental ceramic body is placed. Bismuth, in particular in the form of bismuth oxide, is according to this embodiment only incorporated into the ceramic material by way of exposure to the bismuth containing atmosphere; there is, however, no contact of the body with a bismuth containing substance other than the bismuth containing atmosphere. In particular, there is no direct application of a bismuth containing solution on the dental ceramic body.

The fluorescence intensity to be provided can be adjusted by appropriately choosing the distance between the dental ceramic body and the bismuth source and/or the concentration of bismuth in the bismuth containing atmosphere, which is again governed by the amount of the bismuth compound contained in the bismuth source. Further, it is possible to mask areas of the outer surface of the dental ceramic body at least partially, in order to selectively provide non-fluorescent areas or areas of attenuated fluorescence intensity.

Thus, the process of the present invention allows for a relatively simple adjustment of the fluorescent properties of the dental ceramic body to the actual needs.

Alternatively to the bismuth compound being evaporated in the container, it is also thinkable to produce a bismuth containing gas outside of the container, said gas being then introduced into the container to generate the bismuth containing atmosphere therein.

As mentioned, the container, into which the dental ceramic body or its precursor is placed and in which a bismuth containing atmosphere is generated, is preferably a crucible. Alternatively, it can also be a furnace.

By the use of a crucible as closeable container, a stagnant bismuth containing atmosphere can be obtained even if a relatively moderate amount of bismuth compound in the bismuth source is provided, said atmosphere containing bismuth in a concentration sufficient to allow for bismuth, in particular in the form of bismuth oxide, penetrating into the ceramic body to provide it with the desired fluorescent properties. If exposure to the bismuth containing atmosphere is to be carried out in a conventional furnace, higher amounts of bismuth are necessary to achieve the desired effect, due to the large volume of the furnace and the aeration typically present in the furnace.

The bismuth source containing the bismuth compound to be evaporated can be a liquid bismuth source, in particular containing or essentially consisting of molten bismuth oxide, a solution of bismuth nitrate, specifically bismuth nitrate pentahydrate, and/or a solution of bismuth acetate. In this regard, the liquid bismuth source can in some cases be dried and, hence, become solid before generating the bismuth containing atmosphere. Alternatively, a bismuth source can be used, which ab initio is solid, in particular bismuth-infiltrated zirconia and/or alumina.

According to a preferred embodiment, the crucible confines an inner space having a volume in the range from 50 to 200 cm$^3$, typically of about 100 cm$^3$.

The container, and specifically the crucible, can for example be made of alumina, platinum or a platinum alloy, specifically platinum-rhodium. In particular in view of embodiments, in which the bismuth source contains a relatively high amount of a bismuth compound, the container is preferably made of platinum or a platinum alloy.

Given the high heat-resistance of platinum or a platinum alloy, specifically of platinum-rhodium, a temperature of higher than 1400° C. can be chosen in step c) without negative consequences for the crucible, thereby allowing all of the bismuth compound entering the gas phase, even in the case where a high amount of bismuth compound is provided. Consequently, a container of relatively large volume can be chosen, thereby also allowing to treat multiple dental ceramic bodies in one and the same crucible simultaneously.

In particular in view of treating multiple dental ceramic bodies simultaneously, the bismuth containing source is preferably placed in a central area of the crucible, which upon heating gives rise to a uniform environment for bodies that are equidistantly disposed around the bismuth source.

If necessary or appropriate, the bismuth source can placed in a respective vessel, such as an alumina vessel, arranged in the crucible.

Typically, the bismuth containing atmosphere contains bismuth in the form of bismuth oxide. This is in particular the case when an oxidizing atmosphere, e.g. air, is present, in which bismuth oxide is generated also in the case when the bismuth source contains e.g. bismuth nitrate pentahydrate.

Accordingly, it is further preferred that at least steps b) and c) are performed in the presence of oxygen, and most preferably in the presence of air. In this particular case, the bismuth containing atmosphere relates to air additionally containing bismuth oxide.

According to a particularly preferred embodiment, the atomic mass of bismuth in the bismuth source placed in the container is the range of 0.5 to 1000 mg per liter of volume of the container's inner space.

Accordingly, it is further preferred that the molar concentration of bismuth in the bismuth containing atmosphere is in the range from about $1 \cdot 10^{-6}$ to about $1 \cdot 10^{-2}$ mol/liter, more preferably from about $2 \cdot 10^{-6}$ to about $5 \cdot 10^{-3}$ mol/liter. In this context, the concentration of bismuth relates to any form of bismuth present in the atmosphere, and in particular encompasses bismuth oxide.

It has further been found that the exposure to the bismuth containing atmosphere under step c) of the process of the present invention is preferably performed at a temperature above 1200° C., preferably at a temperature above 1300° C. A temperature at about 1450° C., corresponding to a typical sintering temperature for yttria-stabilized zirconia ceramic, is particularly preferred due to the fact that at this temperature bismuth, in particular in the form of bismuth oxide, efficiently diffuses into the body. At this particularly preferred temperature, there is thus no discoloration which might arise when a relatively high amount of bismuth is deposited on the ceramic without diffusing into the body and therefore accumulating on the outer surface of the body, rather than being incorporated in the body.

As mentioned above, fluorescence is according to the present invention provided by bismuth, specifically in the form of bismuth oxide, penetrating into the dental ceramic body and thereby becoming incorporated into the ceramic material.

The depth of penetration of bismuth, in particular in the form of bismuth oxide, is preferably 500 μm at most, more preferably 400 μm at most, most preferably 300 μm at most. According to a specific embodiment, the depth of penetration is in the range from 200 μm to 250 μm.

As also mentioned above, the providing of fluorescence is preferably integrated in the sintering step and/or at least one of the post-sintering steps normally performed when preparing the dental ceramic body. According to a particularly preferred embodiment, steps b) and c) are performed during sintering the dental ceramic body and/or during a post-sintering step, since this allows a fluorescent ceramic body to be obtained in a most time-saving manner. In this regard, the performing of steps b) and c) during the sintering step is of particular relevance, since at the sintering temperature a highly efficient penetration of bismuth, specifically in the form of bismuth oxide, is achieved.

According to a specifically preferred embodiment, the present invention thus relates to a process comprising the steps of providing fluoresence to a dental ceramic body by treating at least a portion of the outer surface of the dental ceramic body or a precursor thereof with a bismuth containing substance, characterized by the steps of α) placing a precursor of the dental ceramic body thereof into a sintering crucible;

β) generating a bismuth containing atmosphere in the sintering crucible and

γ) sintering the precursor to the dental ceramic body whereby at least a portion of the outer surface of the precursor is exposed to the bismuth containing atmosphere.

Alternatively, it can also be preferred to perform steps b) and c) during a post-sintering step, and more particularly during the final post-sintering step. This is in particular the case when the lower temperature present during the post-sintering steps is sufficient for an efficient incorporation of bismuth and if loss of bismuth already incorporated into the ceramic material, which potentially can occur during heat treatment, shall be diminished.

Since fluorescence is according to the described process obtained by bismuth, in particular in the form of bismuth oxide, penetrating into the dental ceramic body and since the fluorophor is therefore only present in a surface-near region reaching down from the surface to the depth of penetration, the body is particularly well suited for applications for which no or only unsubstantial further machining is required in order obtain the final dental article. This can e.g. be the case if the final dental article is a prosthetic element, the shape of which corresponds essentially to the form of the densily sintered dental ceramic body.

For these applications, pre-sintered blocks are typically pre-shaped with the aid of CAD/CAM systems into the shape of the prostethic element, but having a size 25 to 30% higher than the final element to compensate for the sintering shrinkage. The final sintering temperature is between 1350° C. and 1550°. Apart from bismuth or the bismuth containing compound penetrating into the body, this processing reduces the level of tension present and prevents the transformation from the tetragonal phase to the monoclinic phase, which leads to a final surface virtually free of the monoclinic phase.

According to a further preferred embodiment of the process, the dental ceramic body to which fluorescence is to be provided is, therefore, a dental article, preferably an implant or a prosthetic element for use in a dental restoration, more preferably a crown, a bridge, an abutment, an onlay and/or an inlay.

The relevance of the dental ceramic body for use as a dental implant can be explained by the fact that any loss of natural bone structure, e.g. as a result of bone resorption, can result in soft-tissue shrinkage due to the lack of boney support, which ultimately can lead to the situation that a portion of the implant becomes visible. Since the dental implant according to the present invention can both in colour and luminescence be closely adapted to the colour and luminescence of a natural tooth, an unestethic situation can be circumvented also under these circumstances.

In addition to the process described above, the present invention further relates to a dental ceramic body obtainable by the process.

In this regard, the present invention specifically relates to a dental ceramic body based on zirconia and/or alumina comprising or essentially consisting of
   a core region being at least essentially free of bismuth and
   a surface region surrounding the core region and containing bismuth,
   characterized in that the surface region in which bismuth is contained reaches down from the surface to a depth of 500 µm at most.

Given the fact that bismuth is only contained in a surface region, but is in essence absent from the remainder of the body, any impact of the change in the material on the body's mechanical properties can be kept to a minimum.

In restricting the presence of bismuth to the surface region, i.e. down to a depth of 500 µm at most, the present invention is in clear contrast to technologies, which aim at a relatively deep penetration of the fluorescing agent. In particular, the present invention is in contrast to the technology taught in WO 2014/164199, according to which an open pore structure is required for suffienctly absorbing the solution comprising the colouring and the fluorescing agent and thus to achieve a penetration depth of 5 mm.

In contrast to the penetration depth aimed at in WO 2014/164199, a much lower penetration depth of 500 µm at most is achieved according to the process of the present invention, due to the bismuth diffusing from the gas phase into the body, rather than by being contained in a solution that is absorbed by the body.

If step c) of the process of the present invention is carried out during sintering, a penetration depth of 500 µm at most can be achieved when applying common sintering temperatures, and in particular a temperature of about 1450° C., given that the densification of the material during sintering takes place relatively rapidly. Thus, the skilled person, who has become aware of the inventive process and its preferred embodiments, readily knows how to prepare the dental ceramic body.

As a result of the lower penetration depth, the dental ceramic body of the present invention allows to eliminate fluorescent properties in selected areas of the body in a very simple manner. Specifically, this can be achieved by removing material from the surface region or a portion thereof in the respective areas of the body.

Since by the process of the present invention bismuth diffuses into the material of the body, a concentration gradient within the surface region is typically obtained. Specifically, the concentration of bismuth decreases in direction from the surface of the body towards its core region in a gradual manner. Due to this concentration gradient, the present invention further allows attenuating the fluorescence intensity of the body by partially removing the material from the surface region. In other words, material can be abraded down to a depth, at which the amount of bismuth is low enough for providing the desired attenuated fluorescence intensity.

In contrast to the body obtained according to WO 2014/164199, the dental ceramic body of the present invention allows for a post-processing in order to further adjust the fluorescent properties of the body.

Preferably, the molar amount of bismuth contained in the surface region is less than 0.5 mol-%, preferably less than 0.4 mol-%, more preferably less than 0.3 mol-%, and most preferably less than 0.2 mol-%. Although sufficient for providing the desired fluorescent properties to be dental ceramic body, these amounts are still low enough to further decrease any potential impact on the mechanical properties of the material.

It is further preferred that the amount of bismuth contained in the surface region is higher than 0.06 mol-%, preferably higher than 0.08 mol-%, more preferably higher than 0.1 mol-%, in order to provide sufficient fluorescence to the body.

As mentioned, the dental ceramic body is particularly well suited for applications for which no or only unsubstantial further machining is required in order obtain the final dental article. In particular, the dental ceramic body is a prosthetic element for use in a dental restoration, preferably a crown, a bridge, an implant, an abutment, an onlay and/or an inlay.

Alternatively to the embodiment, in which step c) is carried out during sintering, the process of the present invention also encompasses the embodiment, in which the dental ceramic body or a precursor of the dental ceramic body is exposed to the bismuth containing atmosphere in step c), said dental ceramic body or precursor being non-densified and/or porous. In terms of a sintering process, a green body or a brown body of the dental ceramic body can be subjected to the exposure according to step c). The term "brown body" thereby relates to the green body after burning off the binder.

In other words, step c) can be performed prior to the actual sintering step. Given the lower density of the material in comparison to the densified material obtained during sintering, bismuth can diffuse deeper into the porous ceramic body or precursor. When choosing a sufficiently long time of exposure, this can lead to the point at which bismuth is distributed throughout the whole porous ceramic body or precursor, which can then be subjected to the final sintering at a higher temperature to obtain the dense ceramic body.

For this alternative embodiment, the temperature of step c) is preferably above the evaporating temperature of the bismuth compound, but below the final sintering temperature of the ceramic, and specifically is in a range from 1100° C. to 1200° C.

The present invention, thus, also relates to a dental ceramic block obtainable by the process specified above, the bismuth contained being distributed throughout the whole block. This dental ceramic block can either be non-densified, i.e. in the pre-sintered state, or densified, i.e. in the sintered state.

Specifically, the present invention relates to a dental ceramic block containing bismuth distributed throughout the whole block, the amount of bismuth being higher than 0.06 mol-%, preferably higher than 0.08 mol-%, more preferably higher than 0.1 mol-%.

The features, which in the context of the process and the dental ceramic body of the present invention have been presented as preferred, are likewise preferred features of the dental ceramic block and of the process for preparing the dental ceramic block, respectively. In particular, the dental ceramic block is likewise based on zirconia and/or alumina, as discussed in the context of the process.

Whereas for some applications the dental ceramic body is particularly well suited for applications for which no or only unsubstantial further machining is required in order obtain the final dental article, there are some applications, in which the final dental article is obtained by milling a block of the dense ceramic material. This can e.g. be the case for a dental implant. Apart final dental articles, such as prosthetic elements for use in a dental restoration, dental implants, individualized abutments or complete dentures, the term "dental ceramic body" also ecompasses dental ceramic blocks, in particular semi-finished blocks or blanks, in particular blanks with pre-fabricated connections and block for further chair-side modifications.

For applications, in which the final dental article is obtained by milling a block of the dense ceramic material, the methods according to WO 2013/022612 and WO 2014/164199 are unsuitable, since by the milling the surface near region containing the fluorescent compound is lost.

In particular with regard to a dental ceramic body which after sintering is to be milled into the final dental article, more particularly a dental implant, it would thus be desirable to provide a process for providing a fluorescent dental ceramic material which even after milling maintains its fluorescent properties.

According to a second aspect, the problem to be solved by the present invention is to provide a process for providing a fluorescent dental ceramic body which after milling body into the final dental article maintains its fluorescent properties.

The problem of this second aspect is solved by the process for providing a fluorescent dental ceramic body disclosed herein.

The present invention thus also relates to a process for providing a fluorescent, dense ceramic body based on zirconia and/or alumina comprising the steps of
A) providing a ceramic precursor powder containing apart from zirconia and/or alumina, respectively, bismuth oxide in an amount of lower than 0.7 mol-%, and a binder.
B) pressing the ceramic precursor powder to form a green body,
C) debinding the green body obtained in B) to form a porous brown body, and
D) sintering the porous brown body obtained in C) to obtain the fluorescent, dense ceramic body.

As mentioned above, the ceramic is preferably zirconia, more preferably yttria-stabilized zirconia.

In this regard, the ceramic precursor powder can specifically be a zirconia powder to which bismuth-doped yttria powder is admixed. In this specific case, bismuth diffuses out of the bismuth-doped yttria during sintering, which results in the doping of the yttria-stabilized zirconia.

Alternatively, the ceramic precursor powder can be prepared by admixing a bismuth containing solution to the yttria-stabilized zirconia powder, which likewise results in the doping of the yttria-stabilized zirconia.

According to the invention, bismuth oxide is contained in the ceramic precursor powder in an amount of lower than 0.7 mol-%. In this regard, it is particularly preferred that the amount of bismuth oxide is high enough to provide the desired fluorescent properties, but low enough not to interfere substantially with the colour of the ceramic body to be provided.

In particular in view of providing sufficient fluorescence to be seen by the human eye, the amount of bismuth oxide contained in the ceramic precursor powder is preferably higher than 0.06 mol-%, more preferably higher than 0.08 mol-%, most preferably higher than 0.1 mol-%. Thus, the amount of bismuth or bismuth oxide being used as a fluorophor is higher than if it was used for the sole purpose of providing a defined colour to the material, as it is taught in FR 2 781 366 A1, according to which the amount of bismuth oxide is in any case to be kept below 0.2 wt.-%, i.e. well below 0.06 mol-%, since this is an essential feature of its teaching.

The ceramic precursor powder according to A) can, thus, in particular be referred to as bismuth-doped zirconia, more particularly bismuth-doped yttria-stabilized zirconia.

Bismuth-doped yttria-stabilized zirconia exhibits a particularly high emission intensity, which—without wanting to be bound by the theory—can be explained by the fact that in the final dense ceramic body the main crystalline phase is doped, i.e. the stabilized zirconia, rather than the yttria, which is contained in much lower concentration. Also with regard to the bismuth-doped yttria-stabilized zirconia obtainable by the process according to the second aspect, the tetragonal phase stability of zirconia is not influenced in a negative way by the doping with bismuth.

Specifically, bismuth oxide is not used in a colouring filling material for the purpose of providing a defined colour to the ceramic body. According to this specific embodiment, bismuth-doping serves the sole purpose for providing fluorescence to the ceramic body. In analogy to the above and in further distinction to the teaching of FR 2 781 366 A1, the ceramic precursor powder is preferably devoid of iron (Fe), in order to prevent quenching of the fluorescent properties provided by bismuth.

In the dental ceramic body obtained by this process, the fluorophor bismuth is homogeneously distributed throughout the volume of the body. After milling, i.e. after subtraction of the surface region in at least a portion of the body, the fluorescent properties are fully maintained.

This is of particular relevance for preparing a dental implant or a dental implant abutment made of a fluorescent ceramic material, as the implant or abutment is typically obtained by milling it from a dental ceramic block.

Accordingly, it is preferred that the process further comprises step

E) milling the dental ceramic body to a dental article, in particular to a dental implant or a dental implant abutment.

As the case may be, step C) can further comprise the sub-step of pre-sintering the green body after debinding. Thus, an intermediate body with good machinability is achieved, which can in particular be preferred in view of the preparation of a dental implant or a dental implant abutment.

Preferably, the sintering of D) is carried out in the presence of a bismuth containing atmosphere. Thus, the bismuth oxide vapour pressure can be maintained suffienctly high in order to diminish or prevent diffusion of bismuth out of the ceramic material.

With regard to the composition and to the generation of the bismuth containing atmosphere, the features which have been described as preferred for the process according to the first aspect likewise are preferred for the process according to the second aspect.

Also with regard to the material of the dental ceramic body, the features described as preferred for the process of the first aspect are likewise preferred for the process of the second aspect.

As mentioned, the amount of bismuth contained in the dental ceramic body achieved by the process of the first aspect or by the process of the second aspect is in particular higher than 0.06 mol-%, preferably higher than 0.08 mol-%, more preferably higher than 0.1 mol-%. Further, the amount of bismuth contained in the dental ceramic block is in particular lower than 0.7 mol-%, preferably lower than 0.5 mol-%, more preferably lower than 0.3 mol-%.

The present invention thus also relates to a dental ceramic body, specifically to a dental ceramic block as well as to a final dental article, containing bismuth in an amount of higher than 0.06 mol-%, preferably higher than 0.08 mol-%, more preferably higher than 0.1 mol-%, based on the total composition.

Figure 2:
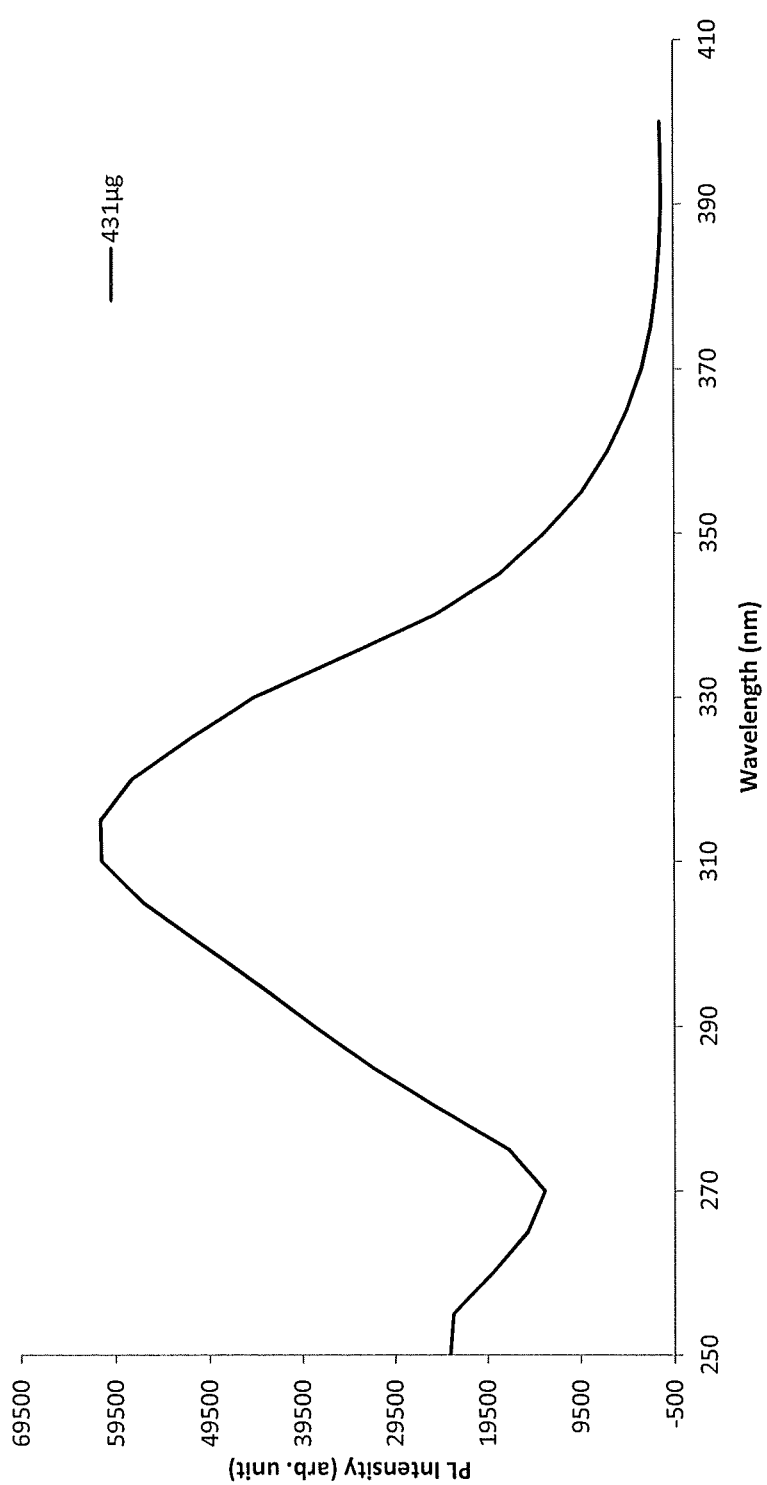

The present invention is exemplified and illustrated by way of the following examples in combination with attached FIG. 1 showing the emission spectra (for an excitation wavelength of 365 nm) of various samples prepared according to the process of the present invention invention; and FIG. 2 showing the excitation spectrum (for an emission wavelength of 460 nm) of a sample prepared according to the process of the present invention invention.

EXAMPLES

Example 1

Relating to the First Aspect of the Present Invention 1.1 g of partially stabilized zirconia powder containing 3.0 mol % ytrria (Tosoh TZ-3YSB-E) was pressed with 65 kN (resulting in a pressure of 171 MPa) to a disc-shaped green body having a diameter of 22 mm.

The resulting green body was then subjected to a heat treatment for debinding (at about 300° to 350° C.) and burning the carbon residues (at about 700° C.), followed by pre-sintering at 1050° C.

The pre-sintered body was then placed in a crucible together with predefined amounts of a bismuth compound, namely of 1% bismuth nitrate in nitric acid (obtained by adding 100 mg of bismuth nitrate pentahydrate to 10 ml of 1% nitric acid) or of bismuth (III) oxide.

Specifically, an alumina vessel having the shape of a hollow cylinder with an outer diameter of 20.5 mm and a height of 18 mm was put into a crucible with inner dimensions of 42×92×25.8 mm. The vessel was placed in a region of the crucible other than the region where the pre-sintered body was placed.

For each of the samples, different amounts of bismuth nitrate or bismuth (III) oxide were given into the alumina vessel and, in case of the bismuth nitrate being in solution, were dried in a drying chamber. The respective amounts are given in Table 1:

TABLE 1

| Sample No. | Bismuth compound | Mass of bismuth compound | Volume of solution (µl) | Atomic mass of Bi (µg) |
|---|---|---|---|---|
| 1 | Bismuth nitrate | 0.1 | 10 | 43.08 |
| 2 | Bismuth nitrate | 0.5 | 50 | 215.41 |
| 3 | Bismuth nitrate | 1.0 | 100 | 430.82 |
| 4 | Bismuth nitrate | 2 | | 861.65 |
| 5 | Bismuth nitrate | 5 | | 2154.12 |
| 6 | Bismuth nitrate | 7 | | 3015.76 |
| 7 | Bismuth nitrate | 8 | | 3446.59 |
| 8 | Bismuth oxide | 10 | | 8969.90 |
| 9 | Bismuth oxide | 100 | | 89699.3 |

Sintering of the pre-sintered body was then performed in the presence of a bismuth containing atmosphere generated from evaporation of the bismuth compound. Specifically, dwelling was performed at a sinter temperature of 1450° C. for 2 hours.

As shown in FIG. 2, sample 3 prepared according to the process of the present invention produced an excitation maximum at 315 nm. As further shown in FIG. 1, the emission maximum produced was at 455 or 460 nm, whereby the highest fluorescence intensity was achieved for the sample using 8.97 mg atomic mass of bismuth (sample 8).

Thus, both the use of bismuth nitrate as well as of bismuth oxide led to the generation of a bismuth-containing atmosphere during the sintering process and consequently to the incorporation of bismuth, specifically in the form of bismuth oxide, in an amount sufficient to impart fluorescent properties closely resembling the one of a natural tooth. Specifically, a bismuth oxide containing atmosphere was generated due to the evaporation of bismuth oxide in one case and to due to the evaporation and oxidation of bismuth nitrate in the other case.

Further experiments have shown that using a zirconia sample infiltrated with a bismuth nitrate solution of higher concentration (100 mg/ml) as bismuth source likewise led to the generation of a bismuth containing atmosphere during sintering.

The visual inspection of the samples under UV-light showed that the upper side of the sample, i.e. the side that was directly exposed to the bismuth-containing atmosphere, was homogeneously doped with bismuth. Thus, a uniform incorporation of bismuth was achieved on this side.

The results shown in FIG. 1 further suggest that the fluorescence intensity is tunable by the amount of bismuth compound put into the crucible and, hence, the concentration of bismuth compound in the bismuth containing atmosphere.

A fluorescence intensity under 365 nm similar to the one of a natural tooth was obtained for an atomic bismuth mass of 3.45 mg in the crucible. Given the volume of about 100 ml of the crucible's inner space, the optimum mass concentration of bismuth was therefore about 0.035 g/l.

Example 2

Relating to the Second Aspect of the Present Invention

Preparation of Bismuth-Doped Yttria

A powder of bismuth doped yttria ($Y_2O_3$:Bi) was prepared by dissolving 19.96 g of yttrium (III) nitrate hexahydrate ($Y(NO_3)_3 \cdot 6\ H_2O$) and urea ($CH_4N_2O$) in nitric acid (10%) and adding 2.15 ml of a solution of bismuth (III) nitrate.pentahydrate ($Bi(NO_3)_3 \cdot 5\ H_2O$) in nitric acid (10 mg/1 ml).

The mixture was then dried at 95° C. in a rotational evaporator at 200 mbar vacuum.

The powder was then fired at 1000° C. for 1 hour in air in an alumina crucible.

The cake received from firing were broken up and crushed to a coarse powder. This powder was washed with deionized water to remove remaining flux and dried in a rotational evaporator. The powder was then sieved with 250 μm mesh.

Preparation of Ceramic Precursor Powder

Zirconia powder TZ-3YSB-E was blended with $Y_2O_3$:Bi. Specifically, two mixtures of 10 g were prepared with either 1 wt.-% or 5 wt.-% of $Y_2O_3$:Bi powder according to Table 2.

TABLE 2

| Sample No. | Percentage $Y_2O_3$:Bi powder (wt-%) | Mass of $Y_2O_3$:Bi powder (g) | Mass of zirconia powder (g) |
|---|---|---|---|
| 10 | 1.0 | 0.1 | 9.9 |
| 11 | 5.0 | 0.5 | 9.5 |

The mixtures were given in mixer beakers and mixed in the speedmixer for 1 minute at 800 rpm.

Samples were then pressed and sintered as described for Example 1 above.

Fluorescence measurments revealed for an excitation wavelength of 365 nm an emission maximum at about 415 nm. The excitation maximum lies at about 328 nm with another maximum at 304 nm.

The invention claimed is:

1. A dental ceramic body based on zirconia and/or alumina comprising:
a core region being at least essentially free of bismuth, and
a surface region surrounding the core region and containing bismuth,
wherein the surface region in which bismuth is contained reaches down from the surface to a depth of 500 μm at most.

2. The dental ceramic body according to claim 1, wherein the molar amount of bismuth contained in the surface region is less than 0.5 mol-%.

3. The dental ceramic body according to claim 1, wherein the dental ceramic body consists essentially of the core region and the surface region.

4. A process for providing a fluorescent dental ceramic body based on zirconia and/or alumina, the process comprising:
A) providing a ceramic precursor powder containing apart from zirconia and/or alumina, respectively, bismuth oxide in an amount that is lower than 0.7 mol-% and higher than 0.06 mol-%, and a binder,
B) pressing the ceramic precursor powder to form a green body,
C) debinding the green body obtained in B) to form a porous brown body, and
D) sintering the porous brown body obtained in C) to obtain the fluorescent dental ceramic body.

5. The process according to claim 4, wherein the sintering of D) is carried out in the presence of a bismuth containing atmosphere.

6. The process according to claim 4, further comprising step E) milling the dental ceramic body to a dental article.

* * * * *